United States Patent [19]

Fehlberg

[11] 4,188,942
[45] Feb. 19, 1980

[54] ENDOSCOPE AND UROLOGICAL INSTRUMENT LOCK

[75] Inventor: David J. Fehlberg, Glendale Heights, Ill.

[73] Assignee: American Hospital Supply Corporation, Evanston, Ill.

[21] Appl. No.: 881,723

[22] Filed: Feb. 27, 1978

[51] Int. Cl.² ............................. A61B 1/00; B25G 3/00
[52] U.S. Cl. ........................................... 128/6; 403/14; 403/330; 285/305
[58] Field of Search ...................... 128/4, 5, 6, 7, 8, 9, 128/247, 303.15; 285/330, 307, 317, DIG. 25, 305; 403/329, 330, 13, 14

[56] References Cited

U.S. PATENT DOCUMENTS

| 839,297 | 12/1906 | Kennedy et al. | 403/329 |
|---|---|---|---|
| 937,437 | 10/1909 | Halstead et al. | 285/317 |
| 949,608 | 2/1910 | Watt | 285/330 |
| 2,431,268 | 11/1947 | McIntyre | 285/317 |
| 2,442,966 | 6/1948 | Wallace | 128/303.15 |
| 2,476,172 | 7/1949 | Williams | 285/317 |
| 3,718,350 | 2/1973 | Klein | 285/DIG. 25 |
| 3,832,075 | 8/1974 | Arai | 403/14 |
| 3,884,587 | 5/1975 | Caldwell | 403/14 |

OTHER PUBLICATIONS

NASA Tech Brief—MFS—21007, —Quick Disconnect Coupling, Positive Locking—Marshall Space Flight Center—Alabama—35812.

Primary Examiner—Robert W. Michell
Assistant Examiner—Arthur S. Rose
Attorney, Agent, or Firm—Tilton, Fallon, Lungmus & Chestnut

[57] ABSTRACT

A two-stage locking or latching mechanism for releasably connecting an endoscope and a urological instrument. In the first latching stage a body portion of the endoscope is fully received within a socket of the urological instrument and is restrained by a cooperating lug and socket against all movement except limited outward axial movement into the second latching stage. In the second latching stage the parts are secured against further axial separation unless they are first rotated with respect to each other to cam a spring out of latching engagement with the body portion of the endoscope.

18 Claims, 8 Drawing Figures

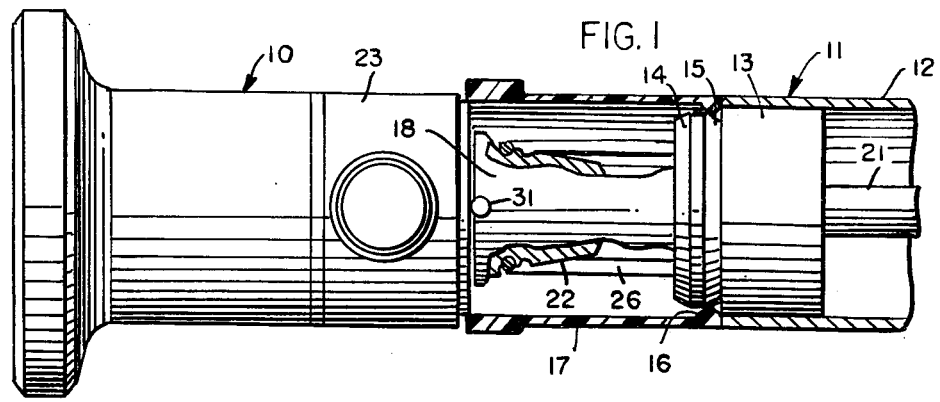
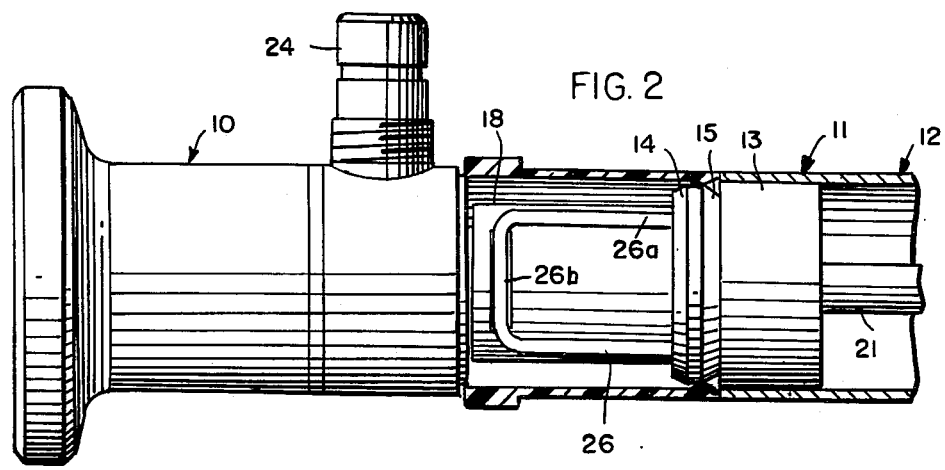
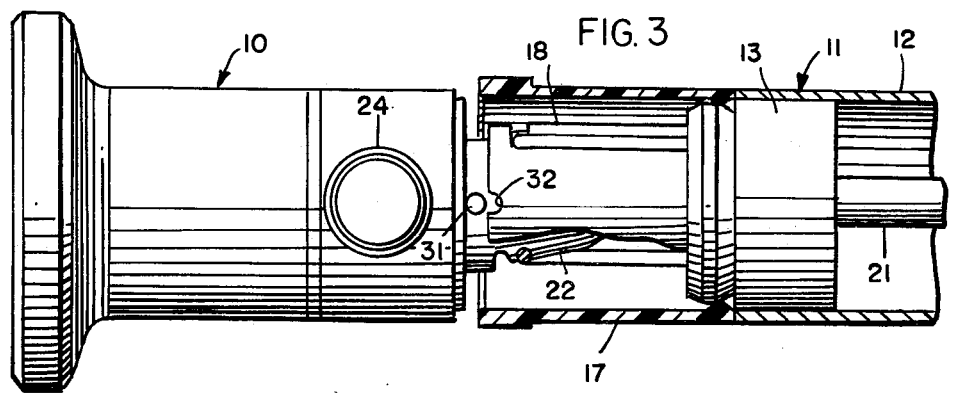
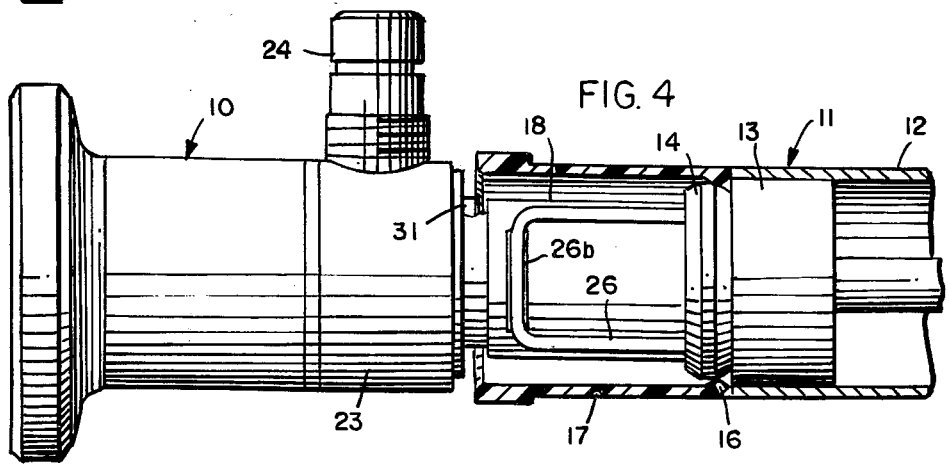

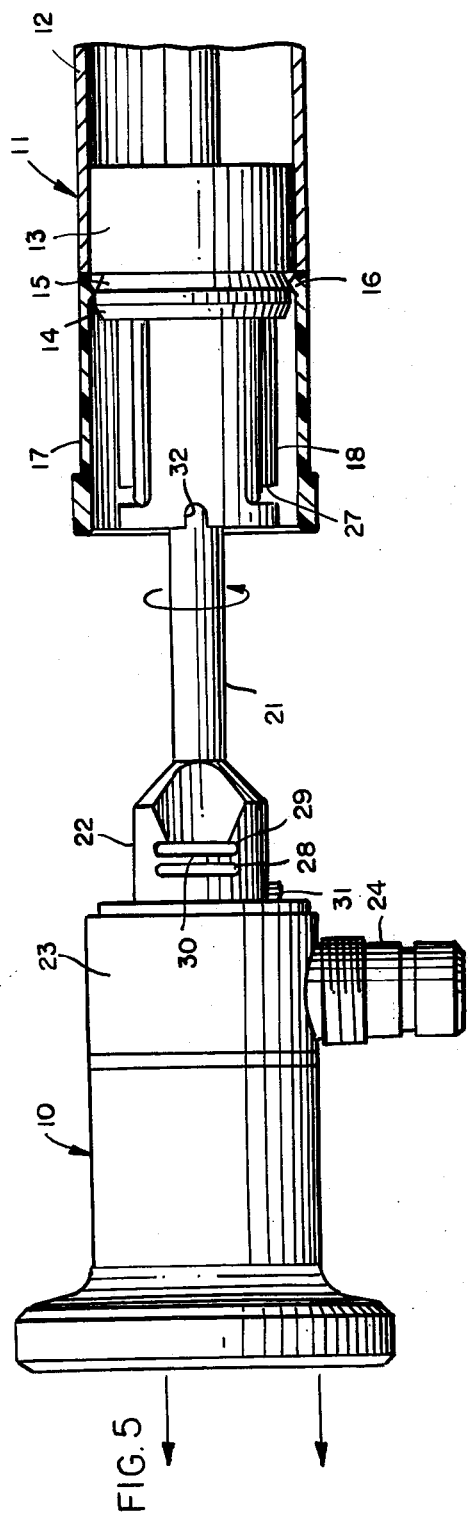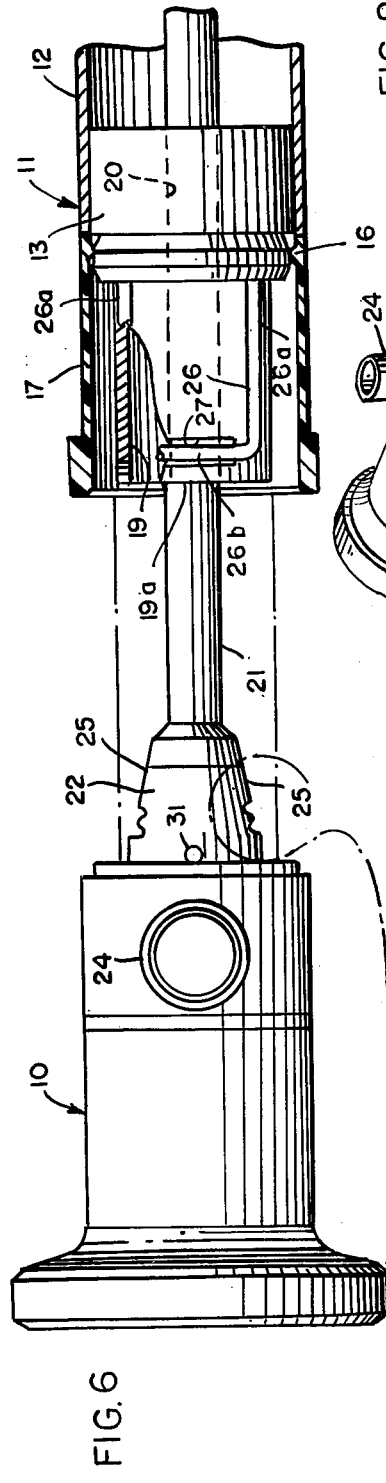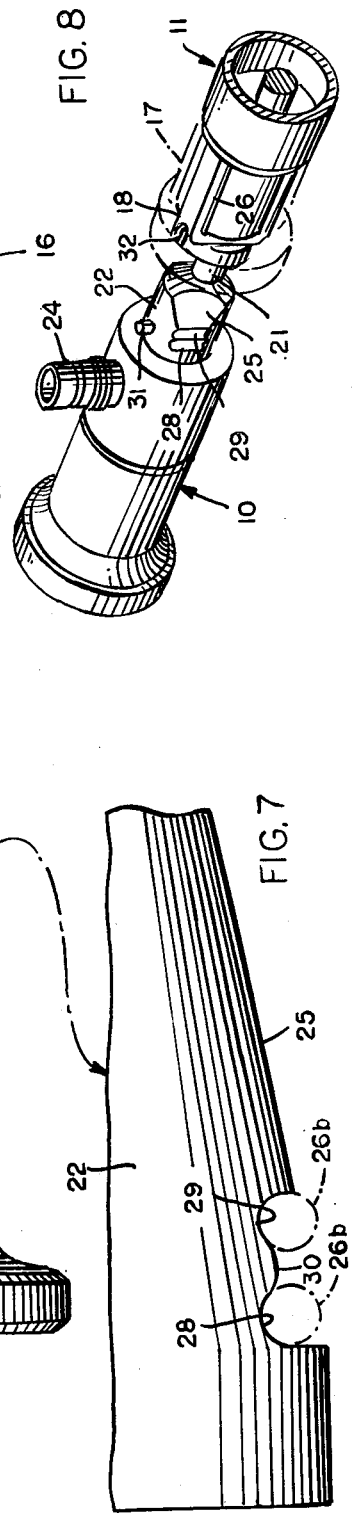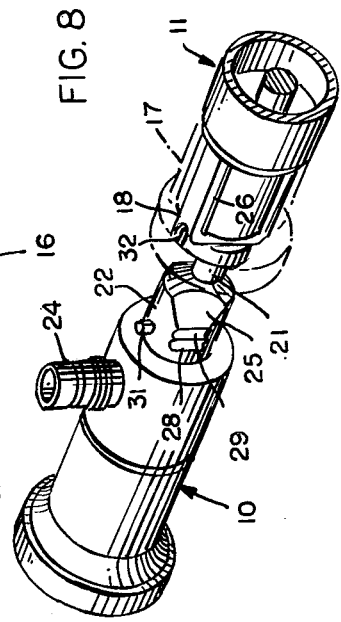

ENDOSCOPE AND UROLOGICAL INSTRUMENT LOCK

BACKGROUND AND SUMMARY

A variety of coupling devices which provide the advantages of quick disconnection are disclosed in the prior art. NASA Tech Brief MFF-21007 discloses a two-piece coupling with a positive locking mechanism intended for use in connection with a soil penetrometer for lunar landing modules and for other applications involving the transmission of axial forces. In the NASA mechanism, a spring wire latch fits into a notch to secure the ends of the coupling against axial separation. Disengagement is achieved by first rotating the parts to release the spring from the notch in which it is received.

While such coupling has the advantages of simplicity in construction and operation, it is unsuitable for use in those applications where the parts must be capable of withstanding twisting forces in use. Couplings which resist release when exposed to rotational forces as well as axial forces tend to be relatively complex, expensive, and bulky. Furthermore, constructions which are designed to prevent inadvertent separation when exposed to rotational as well as axial forces also tend to be difficult to manipulate when intentional disconnection is desired.

Endoscopic instruments used in urological procedures and other medical procedures commonly consist of two main elements: an endoscope (or telescope) and the operating instrument itself. Ease of disassembly of such components is important for purposes of cleaning and repair and to permit utilization of the endoscope (a relatively expensive component) with any of a number of different instruments. On the other hand, it is at least equally important that the parts be latched together so that they are not likely to become inadvertently disengaged during a medical procedure. Prior constructions have not been entirely successful in resisting unintentional separation while achieving ease of intentional disconnection, much less by means which are relatively simple, compact, durable, and reliable in operation.

This invention is concerned with a latching mechanism which overcomes the defects and disadvantages of the prior art. Specifically, the latching mechanism of this invention results in an endoscope-instrument assembly in which twisting forces and other forces commonly encountered in the use of the assembly will not result in disconnection or disorientation of the parts, but one in which disconnection may be easily and quickly accomplished when intentional disassembly is desired. It is also a further object of this invention to provide an endoscope latching mechanism which requires a two-step procedure for unlatching the parts but only a single step procedure for coupling them together.

In brief, the latching mechanism involves a pair of telescoping parts, one of the parts being a generally cylindrical body portion of the endoscope and the other part being a socket-providing tube of the instrument. As used herein, the term "instrument" is intended to refer to any of the instruments commonly associated with an endoscope such as, for example, a urological grasping forceps, a so-called working element, a deflecting bridge as used in urology, etc. Reference may be had to co-pending co-owned applications Ser. Nos. 824,839, filed Aug. 15, 1977, and 838,939, filed Oct. 3, 1977, as illustrations of instruments with which the latching mechanism of this invention may be used.

The socket-providing tube of the instrument has at least one lateral opening into which a section of an externally-mounted spring projects. The body portion of the endoscope disposed within the socket includes a first recess which receives that section of the spring when the two parts are fully connected. In addition, the body portion of the endoscope has a second recess which is spaced axially from the first and which receives the inwardly-protruding section of the spring when the parts are in what may be referred to as a partially latched condition. Means in the form of a lug and a lug-receiving recess serve to lock the endoscope and instrument against relative rotation when the parts are fully latched; hence, the only possible relative movement between the parts when they are fully latched is limited axial movement of the endoscope body into its partially latched position. Further axial separation of the parts is prevented by the section of the spring received in the second recess but if, following such limited axial displacement, the endoscope body is rotated relative to the instrument then the spring section will be cammed out of the second recess to release the endoscope for axial removal from the instrument. Although rotation in the second latching stage (i.e., the partially latched condition) is required for disassembly, no rotation is necessary when reassembly of the components takes place; the endoscope is simply inserted axially into the instrument until the body portion is fully received in its socket.

Other structural features, advantages, and objects of the invention will become apparent from the specification and drawings.

DRAWINGS

FIG. 1 is a fragmentary top plan view taken partly in longitudinal section showing an endoscope and instrument in fully latched condition.

FIG. 2 is a side elevational view taken partly in section of the assembly depicted in FIG. 1.

FIG. 3 is a fragmentary top plan view taken partly in section and similar to FIG. 1 but showing the parts in partially latched condition.

FIG. 4 is a fragmentary side elevational view of the structure depicted in FIG. 3.

FIG. 5 is a fragmentary longitudinal sectional view showing the instrument from the same view as shown in FIGS. 1 and 3 but depicting the endoscope after it has been rotated and displaced axially into unlatched position.

FIG. 6 is a side view of the parts in the relationship shown in FIG. 5.

FIG. 7 is a greatly enlarged view illustrating details of the first and second recesses of the endoscope body.

FIG. 8 is a fragmentary perspective view illustrating the general relationship of parts, a shroud portion of the instrument being shown in phantom for clarity of illustration.

DETAILED DESCRIPTION

Referring to the drawings, and in particular to FIG. 8, the numeral 10 generally designates an endoscope adapted to be coupled to an instrument 11. The instrument may be any of a variety of medical instruments with which endoscopes are commonly used. Reference may be had to the aforementioned co-pending applications, and to the patents identified therein, for more complete disclosures of such instruments. The description of instrument 11 herein will be limited essentially to those features relating directly to the latch mechanism and its method of operation.

Instrument 11 includes a housing 12 equipped at one end with an annular member 13 which may be formed integrally with the housing or, as shown in FIGS. 1-6, secured within the proximal end portion of the housing. The annular member is also provided with a beveled end surface 14 and an annular groove 15 for cooperation with the bead or internal rib 16 of a tubular shroud 17. The shroud is preferably formed of electrically-insulating plastic material which is rigid but nevertheless sufficiently yieldable to allow rib 16 to expand when it is cammed outwardly by beveled surface 14 (when the shroud is fitted into position) or the inclined surface of groove 15 (when the shroud is being removed).

The annular member 13 includes a tube extension 18 which is cylindrical in configuration and which defines a socket 19 having an entrance 19a at the proximal end of the instrument (FIG. 6). As indicated in FIGS. 6 and 8, the cylindrical socket 19 communicates directly with the reduced axial bore 20 of the annular member 13.

The bore 20 slidably receives the stem 21 of endoscope 10. As is well known in the art, the stem contains light- and image-transmitting elements such as glass fiber bundles or rod lenses. The stem terminates at its proximal end in a body 22 in the shape of a modified cylinder, the body in turn being connected to an eyepiece assembly 23. A coupling 24 projects laterally from the eyepiece assembly and is used for the purpose of attaching a fiberoptic cable to the endoscope for supplying light which is then transmitted through the sheath 21, thereby illuminating the area of the body to be examined at the distal end of the endoscope. The image is then transmitted back to eyepiece 23 for viewing by the urologist or other medical practioner.

The cylindrical surface of body 22 is dimensioned to fit smoothly and slidably into socket 19 of instrument tube 18. As shown most clearly in FIGS. 5, 6, and 8, the body is provided with lateral surfaces 25 which converge towards the stem 21 and which constitute cam surfaces for engaging and directing a pair of spring elements 26 carried by instrument 11. Each of the spring elements is generally C-shaped in configuration with its end portions 26a secured to annular member 13 and with its intermediate portion or section 26b normally projecting into socket 19 through one of a pair of lateral openings 27 formed in the wall of tube 18. Thus, as the body 22 of the endoscope is advanced into socket 19 with its sloping surfaces 25 properly oriented relative to the intermediate sections 26b of springs 26, such surfaces will engage the intermediate sections of the springs and urge such sections laterally outwardly within the slots or openings 27 of tube 18.

The body portion 22 of the endoscope is also provided on its opposite sides with a pair of recesses for latching engagement with the intermediate sections of springs 26. Specifically, there is on each side of body 22 a first recess 28 and a second recess 29. Each recess extends in a plane normal to the axis of the body and is both dimensioned and shaped to receive at least a major portion of the cross section of spring section 26b (see FIG. 7). Between the recesses of each pair is a shallow rib 30 which has a transverse dimension substantially less than the full transverse depth of each of the recesses 28 and 29. The result is that when section 26b of each spring is received within one of the recesses 28 or 29, the spring section may be shifted into the other of such recesses by simply exerting an axial force of predetermined magnitude upon the endoscope.

More specifically, when body 22 of the endoscope is fully inserted into socket 19 of instrument tube 18, the transverse intermediate sections 26b of springs 26 will be seated in the first recesses 28. Should an axial force of sufficient magnitude be exerted to urge the endoscope 10 axially away from instrument 11, springs 26 will ride over ribs 30 and will seat in the second recesses 29. In such a condition the endoscope is partially latched. Further axial separation of the parts is firmly resisted because spring sections 26b are too deeply seated in recesses 29.

Referring to FIGS. 3 and 8, it will be observed that the body portion 22 of the endoscope is provided with a projection or lug 31 which extends radially outwardly from the body at the proximal end thereof, that is, at the end remote from sheath 21. The lug is receivable in a slot 32 formed in the wall of tube 18 and extending inwardly from the edge defining the entrance 19a to the socket of that tube. In the embodiment illustrated in the drawings both the lug and the slot are located at the upper limits of their respective components. While such a construction has visual advantages in facilitating assembly of the parts, it will be understood that the lug and slot might instead be positioned along the undersides of the parts or at any other suitable location about the perimeters of the body 22 and tube 18.

When the endoscope body 22 is received within tube 18 in a fully latched position, lug 31 is seated within slot 32 to prevent relative rotation of the endoscope 10 and instrument 11 (FIGS. 1 and 2). The spring arms 26 have their intermediate sections 26b seated in the first recesses 28 to provide limited resistance against axial separation of the parts. The endoscope and instrument are therefore fully latched together in condition for use. If, during such use a twisting force should be applied to the endoscope, as might happen if a pulling force were exerted upon the light-transmitting cable attached to coupling 24, the interfitting lug 31 and slot 32 would resist such movement, thereby maintaining the parts in fully latched condition.

Even axial separation forces will not of themselves be sufficient to disengage the parts for reasons already described. Separation may be achieved only by first moving the endoscope body 22 into its partially latched position in which lug 31 is withdrawn from slot 32 (FIGS. 3 and 4) and thereafter rotating the endoscope 10 in relation to instrument 11 to cause the intermediate portions 26b of spring arms 26 to ride out of secondary recesses 29 and onto the cylindrical surface of body 22. In other words, upon rotating the endoscope approximately 90 degrees relative to the instrument 11, the spring arms are cammed out of recesses 29 to permit axial separation of the parts (FIGS. 5 and 6).

In the embodiment illustrated in the drawings, lug 31 takes the form of a radially-extending cylindrical pin; however, it is to be understood that other lug configurations might be suitable. Also, while a pair of opposing spring arms are disclosed on opposite sides of the socket-providing tube 18, the latching actions described herein might be performed, although perhaps less effectively, by utilizing only a single spring element on one side of the tube. The structure disclosed herein represents a preferred embodiment of the invention and it will be understood by those skilled in the art that many of the details set forth herein might be varied by those skilled in the art without departing from the spirit and scope of the invention.

I claim:

1. A latching mechanism for releasably connecting an endoscope and a urological instrument in operative relation; said latching mechanism including a generally cylindrical body and a tube separate from said body defining a socket; said socket being sized such that it will receive said body; wherein the improvement comprises said socket having at least one opening through a wall portion thereof; a spring mounted externally of said socket and being biased such that a section thereof projects into said socket through said opening; said section being movable out of said socket upon outward flexure of said spring; said body having a first recess positioned and sized such that it will receive said section of said spring when said body is fully inserted into said socket, defining a fully latched position of said body; first cam means for camming said spring section out of said first recess upon the application of a force of predetermined magnitude urging said body axially away from said socket; said body also having a second recess spaced axially from said first recess, said second recess being positioned and sized such that when said body is moved out of said fully latched position and axially away from said socket, said second recess will receive said spring section, defining a partially latched position of said body; means for preventing axial movement of said body away from said socket when said body is in said partially latched position; said body and said socket being further sized such that said body is rotatable with respect to said socket when said body is in said partially latched position; second cam means for camming said spring section out of said second recess when said body is rotated with respect to said socket while said body is in said partially latched position, thereby releasing said body for axial separation from said socket; and locking means provided by said body and said socket for locking said body against rotation in said socket when said body is in its fully latched position.

2. The mechanism of claim 1 in which said locking means comprises a lug provided by one of said socket and body and a slot provided by the other of said socket and body, said lug being received in said slot to block relative rotation of said socket and body only when said body is fully inserted into said socket.

3. The mechanism of claim 2 wherein said lug is provided by said body and said slot is formed in said socket.

4. The mechanism of claim 3 in which said lug extends radially outwardly from said body.

5. The mechanism of claim 3 wherein said socket includes an annular edge defining the entrance to said socket, said slot being formed in said annular edge.

6. The mechanism of claim 5 in which said slot extends axially away from said annular edge.

7. The mechanism of claim 1 in which said first and second recesses extend in planes normal to the axis of said body and are separated by a rib having a transverse dimension less than the full depth of each of said recesses, whereby, axial force above a predetermined magnitude permits said spring section to shift between said first and second recesses as said body is moved axially between its fully and partially latched positions.

8. The mechanism of claim 7 in which said rib has a rounded cross sectional contour.

9. The mechanism of claim 1 in which said body has a free end portion and is tapered to provide a sloping cam surface extending from said end portion to said second recess, said cam surface being engagable with said spring section to guide said section into said second recess as said body is urged into said socket.

10. The combination of an endoscope having a generally cylindrical body and an instrument having a socket removably receiving said body, wherein the improvement comprises said socket having a pair of side openings through the wall thereof; a pair of springs disposed on opposite sides of said socket and being biased such that sections thereof project into said socket through said openings; said sections being movable out of said socket upon outward flexure of said springs; said body having a pair of recesses on opposite sides thereof; each pair of recesses including a first recess positioned and sized such that it will receive said section of one of said springs when said body is inserted into said socket, defining a fully latched position of said body; first cam means for camming said section of each spring out of said first recess upon the application of a force of predetermined magnitude urging said body axially away from said socket; each pair of recesses also including a second recess spaced axially from said first recess, each of said second recesses being positioned and sized such that when said body is moved out of its fully latched position and axially away from said socket each said second recess will receive said section of one of said springs, defining a partially latched position of said body; means for preventing axial movement of said body away from said socket when said body is in said partially latched position; said body and said socket being further sized such that said body is rotatable with respect to said socket when said body is in said partially latched position; second cam means for camming each said section of said springs out of said second recesses when said body is rotated with respect to said socket while said body is in said partially latched position, thereby releasing said body for axial separation from said socket; and means provided by said body and said socket for locking said body against rotation in said socket when said body is in its fully latched position.

11. The combination of claim 10 in which said means comprises a lug provided by one of said socket and body and a slot provided by the other of said socket and body, said lug being received in said slot to block relative rotation of said socket and body only when said body is fully inserted into said socket.

12. The combination of claim 11 in which said lug is provided by said body and said slot is formed in said socket.

13. The combination of claim 12 in which said lug extends radially outwardly from said body.

14. The combination of claim 12 in which said socket includes an annular edge defining the entrance to said socket, said slot being formed in said annular edge.

15. The combination of claim 14 in which said slot extends axially away from said edge.

16. The combination of claim 10 in which said first and second recesses of each pair extend in planes normal to the axis of said body and are separated by a rib having a transverse dimension less than the full depth of each of said first and second recesses, whereby, axial force above a predetermined magnitude permits said sections of said spring to shift between said first and second recesses of each pair as said body is moved axially between its fully and partially latched positions.

17. The combination of claim 16 in which each of said ribs has a rounded cross sectional contour.

18. The combination of claim 10 in which said body is tapered to provide a pair of sloping cam surfaces engagable with said sections of both of said springs to guide said sections into said second recesses as said body is urged into said socket.

* * * * *